United States Patent
Ansari et al.

(10) Patent No.: US 10,034,638 B2
(45) Date of Patent: Jul. 31, 2018

(54) ADAPTIVE EPSILON-TUBE FILTER FOR BLUNT NOISE REMOVAL

(71) Applicant: THE REGENTS OF THE UNIVERSITY OF MICHIGAN, Ann Arbor, MI (US)

(72) Inventors: Sardar Ansari, Richmond, VA (US); Kayvan Najarian, Northville, MI (US); Kevin Ward, Superior Township, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 206 days.

(21) Appl. No.: 15/049,653

(22) Filed: Feb. 22, 2016

(65) Prior Publication Data
US 2016/0287180 A1    Oct. 6, 2016

Related U.S. Application Data

(60) Provisional application No. 62/142,593, filed on Apr. 3, 2015.

(51) Int. Cl.
*A61B 5/00* (2006.01)
*A61B 5/021* (2006.01)
(Continued)

(52) U.S. Cl.
CPC .............. *A61B 5/721* (2013.01); *A61B 5/021* (2013.01); *A61B 5/031* (2013.01); *A61B 5/0402* (2013.01);
(Continued)

(58) Field of Classification Search
CPC ....... A61B 5/021; A61B 5/031; A61B 5/0402; A61B 5/0535; A61B 5/0836; A61B 5/721;
(Continued)

(56) References Cited

U.S. PATENT DOCUMENTS 5,603,321 A    2/1997    Kynor et al.
5,853,364 A    12/1998    Baker et al.
(Continued)

OTHER PUBLICATIONS

International Preliminary Report on Patentability, International Patent Application No. PCT/US2016/018911, dated Oct. 3, 2017.
(Continued)

*Primary Examiner* — George Manuel
(74) *Attorney, Agent, or Firm* — Marshall, Gerstein & Borun LLP

(57) ABSTRACT

Techniques for motion artifact (MA) reduction in impedance plethysmography (IP) and other physiological signals are provided. The techniques limit the amplitude of MA filtered signals by imposing an "ε-tube." The techniques may include the introduction of a regularization term to ensure that the pattern of a filtered signal is similar to the pattern of the primary component of the original, unfiltered signal by maximizing the regularity of the filtered signal. The techniques may be integrated into a portable monitoring device, such as an armband, to remove MA from various diagnostic signals and to extract primary signal components for producing enhanced device performance.

30 Claims, 6 Drawing Sheets

(51) Int. Cl.
  *A61B 5/03*    (2006.01)
  *A61B 5/0402*  (2006.01)
  *A61B 5/053*   (2006.01)
  *A61B 5/083*   (2006.01)
  *A61B 8/08*    (2006.01)

(52) U.S. Cl.
  CPC .......... *A61B 5/0535* (2013.01); *A61B 5/0836* (2013.01); *A61B 5/725* (2013.01); *A61B 5/7214* (2013.01); *A61B 5/7253* (2013.01); *A61B 8/488* (2013.01); *A61B 8/5223* (2013.01); *A61B 8/5269* (2013.01); *A61B 8/5276* (2013.01)

(58) Field of Classification Search
  CPC ..... A61B 5/7214; A61B 5/725; A61B 5/7253; A61B 8/488; A61B 8/5223; A61B 8/5269; A61B 8/5276
  See application file for complete search history.

(56) References Cited

U.S. PATENT DOCUMENTS

| | | | |
|---|---|---|---|
| 5,924,980 | A | 7/1999 | Coetzee |
| 8,755,877 | B2 | 6/2014 | Zoica |
| 2004/0073125 | A1 | 4/2004 | Lovett et al. |
| 2006/0258927 | A1 | 11/2006 | Edgar et al. |
| 2010/0198097 | A1 | 8/2010 | Sowelam |
| 2011/0004069 | A1 | 1/2011 | Ochs et al. |
| 2011/0075514 | A1* | 3/2011 | Barajas-Olalde ...... G01V 1/364 367/43 |
| 2013/0324812 | A1 | 12/2013 | Brainard, II et al. |
| 2014/0073958 | A1 | 3/2014 | Rodriguez-Llorente et al. |
| 2014/0275854 | A1* | 9/2014 | Venkatraman ......... A61B 5/721 600/301 |

OTHER PUBLICATIONS

Goodyear et al., Filtering noise from fMRI data using the stockwell transform, Proc. Intl. Mag. Reson. Med., 10: (2002).
International Search Report and Written Opinion, International Application No. PCT/US16/18911, dated Jul. 26, 2016.
Ansari et al., "Epsilon-Tube Filtering: Reduction of High-Amplitude Motion Artifacts from Impedance Plethysmography Signal," IEEE Journal of Biomedical and Health Informatics, vol. 19, No. 2, Mar. 2015, pp. 406-417.
Ansari et al., "Tube Regression: A New Method for Motion Artifact Reduction," 33rd Annual International Conference of the IEEE EMBS, Boston, MA, Aug. 30-Sep. 3, 2011, pp. 2736-2739.
Ansari et al., Motion artifact suppression in impedance pneuomgraphy signal for portable monitoring of respiration: an adaptive approach, IEEE J. Biomedical Health Informatics, 11 pp. (Feb. 3, 2016).
Asada et al., Active noise cancellation using mems accelerometers for motion-tolerant wearable bio-sensors, Engineering in Medicine and Biology Society, 2004. IEMBS'04. 26th Annual International Conference of the IEEE, vol. 1. pp. 2157-2160 (2004).
Barros et al., Removing artifacts from electrocardiographic signals using independent components analysis, Neurocomputing, 22(1-3):173-86 (1998).
Chan et al., Adaptive reduction of motion artifact from photoplethysmographic recordings using a variable step-size LMS filter, Sensors, 2002, Proceedings of the IEEE, vol. 2, pp. 1343-1346 (2002).
Chawla, PCA and ICA processing methods for removal of artifacts and noise in electrocardiograms: A survey and comparison, Appl. Soft Computing, 11(2):2216-26 (2011).
Hamilton et al., Adaptive removal of motion artifact, Engineering in Medicine and Biology Society, Proceedings of the 19th Annual International Conference of the IEEE, vol. 1, pp. 297-299 (1997).
Hamilton et al., Comparison of methods for adaptive removal of motion artifact, Computers in Cardiology, pp. 383-386 (2000).
Han et al., Development of real-time motionartifact reduction algorithm for a wearable photoplethysmography, Engineering in Medicine and Biology Society, EMBS 2007, 29th Annual International Conference of the IEEE, pp. 1538-1541 (2007).
International Search Report for International application No. PCT/US2014/069124, dated Sep. 22, 2015.
International Preliminary Report on Patentability, International Application No. PCT/US2014/069124, dated Jun. 7, 2016.
Jeong et al., Development of a technique for cancelling motion artifact in ambulatory ECG monitoring system, ICCIT '08: Third International Conference on Convergence and Hybrid Information Technology, vol. 1, pp. 954-961 (2008).
Khambete et al., Movement artefact rejection in impedance pneumography using six strategically placed electrodes, Physiological measurement, vol. 21, No. 1, p. 79 (2000).
Kim et al., Motion artifact reduction in photoplethysmography using independent component analysis, IEEE Trans Biomedical Engineering, 53(3):566-8 (2006).
Lee et al., Design of filter to reject motion artifact of pulse oximetry, Computer Standards & Interfaces, 26(3):241-9 (2004).
Lee et al., Improved elimination of motion artifacts from a photoplethysmographic signal using a Kalman smoother with simultaneous accelerometry, Physiological Measurement, 31(12):1585 (2010).
Lee et al., Reduction of motion artifacts from photoplethysmographic recordings using a wavelet denoising approach, IEEE EMBS Asian-Pacific Conference on Biomedical Engineering, pp. 194-195 (2003).
Liu et al., Motion artifact reduction in electrocardiogram using adaptive filter, J. Med. Biol. Engineering, 31(1):67-72 (2011).
Luo et al., Experimental study: brachial motion artifact reduction in the ECG, Computers in Cardiology, pp. 33-36 (1995).
Luo et al., The electrode system in impedance-based ventilation measurement, IEEE Trans. Biomedical Engineering, 39(11):1130-41 (1992).
Milanesi et al., Independent component analysis applied to the removal of motion artifacts from electrocardiographic signals, Medical & Biological Engineering & Computing, 46(3):251-61 (2008).
Milanesi et al., Multichannel Techniques for Motion Artifacts Removal from Electrocardiographic Signals, Engineering in Medicine and Biology Society, EMBS '06: 28th Annual International Conference of the IEEE, pp. 3391-3394 (Aug. 30-Sep. 3, 2006).
Rahman et al., An efficient noise cancellation technique to remove noise from the ECG signal using normalized signed regressor LMS algorithm, Bioinformatics and Biomedicine, BIBM '09 IEEE International Conference on IEEE, pp. 257-260 (2009).
Raya et al., Adaptive noise cancelling of motion artifactin stress ECG signals using accelerometer, Engineering in Medicine and Biology, 2002. 24th Annual Conference and the Annual Fall Meeting of the Biomedical Engineering Society EMBS/BMES Conference (IEEE), vol. 2., pp. 1756-1757 (2002).
Reddy et al., Motion artifact reduction in photoplethysmographic signals using singular value decomposition, IMTC 2007: Instrumentation and Measurement Technology Conference Proceedings of, pp. 1-4 (2007).
Reddy et al., Use of Fourier series analysis for motion artifact reduction and data compression of photoplethysmographic signals, IEEE Trans. Instrumentation and Measurement, 58(5): 1706-11 (2009).
Rosell et al., Reduction of motion artifacts using a two-frequency impedance plethysmograph and adaptive filtering, IEEE Trans. Biomedical Engineering, 42(10):1044-8 (1995).
Rosell et al., Signal-to-motion artifact ratio versus frequency for impedance pneumography, IEEE Trans. Biomedical Engineering, 42(3):321-3 (1995).
Sahakian et al., Electrode Motion Artifacts in Electrical Impedance Pneumography, IEEE Trans on Biomedical Engineering, BME-32(6):448-51 (1985).

(56) References Cited

OTHER PUBLICATIONS

Seppa et al., Novel electrode configuration for highly linear impedance pneumography, Biomedizinische Technik/Biomedical Engineering, 59(1):35-8 (2013).
Seyedtabaii et al., Kalman filter based adaptive reduction of motion artifact from photoplethysmographic signal, Proceedings of World Acadmy of Science, Engineering and Technology, vol. 27 (2008).
Tong et al., Adaptive reduction of motion artifact in the electrocardiogram, Engineering in Medicine and Biology, 24th Annual Conference and the Annual Fall Meeting of the Biomedical Engineering Society EMBS/BMES Conference, vol. 2, pp. 1403-1404 (2002).
Wood et al., Low variance adaptive filter for cancelling motion artifact in wearable photoplethysmogram sensor signals, Engineering in Medicine and Biology Society, EMBS 2007, 29th Annual International Conference of the IEEE, pp. 652-655 (2007).
Written Opinion for International application No. PCT/US2014/069124, dated Sep. 22, 2015.
Yan et al., Reduction of motion artifact in pulse oximetry by smoothed pseudo Wigner-Ville distribution, J. Neuroengineering and Rehabilitation, 2(3):1-9 (2005).
Yoon et al., Adaptive motion artifacts reduction using 3-axis accelerometer in E-textile ECG measurement system, J. Med. Systems, 32(2):101-6 (2008).
Liu et al., Reduction of motion artifacts in electrocardiogram monitoring using an optical sensor, Biomedical Instrumentation & Technology, 2:155-63 (2011).
Ottenbacher et al., Reliable motion artifact detection for ECG monitoring systems with dry electrodes, 30th Annual International IEEE EMBS Conference, Vancouver, British Columbia, Canada, Aug. 20-24, 2008.

\* cited by examiner

ADAPTIVE EPSILON-TUBE FILTER FOR BLUNT NOISE REMOVAL

CROSS-REFERENCE TO RELATED APPLICATION

This application claims the priority benefit under 35 U.S.C. § 119(e) of U.S. Provisional Patent Application No. 62/142,593, filed Apr. 3, 2015, the disclosure of which is incorporated herein by reference in its entirety.

STATEMENT OF GOVERNMENTAL INTEREST

This invention was made with government support under a Phase I STTR (W81XWH-08-C-0115) and a Phase II STTR (W81XWH-09-C-0117), awarded by the U.S. Army. The Government has certain rights in the invention.

FIELD OF INVENTION

The present disclosure generally relates to systems, methods, apparatus, and non-transitory media for filtering signals and, more particularly, to filtering signals by removing blunt noise that is mixed with the signals.

BACKGROUND

For patients suffering from a variety of injuries or disease states such as venous thrombosis, burns, trauma, various types of heart conditions, sepsis, various types of encephalopathy, dehydration, renal failure, dialysis, hypertension, neuromuscular diseases, low-back pain, motor control disorders, etc., signals generated via relevant medical diagnostic equipment may provide valuable insight for medical professionals.

However, in many medical diagnostic examinations, a diagnostic signal generated by the relevant diagnostic equipment may include noise and/or artifacts. Noise and/or artifacts may be introduced into the diagnostic signal due to a presence of one or more extraneous factors that may influence the diagnostic signal while the test is being performed, such as the patient's movement during the test, electrical noise, etc. In some cases, the amplitude of the noise may be larger than the amplitude of the diagnostic signal, and the frequency components of the noise may largely overlap with those of the diagnostic signal. As a result, conventional filtering methods may attenuate or distort the diagnostic signal, or fail to model the noise adequately and effectively. In addition, conventional attempts to remove artifacts from diagnostic signals using multi-channel recordings of the diagnostic signal, such as independent component analysis (ICA), may add unwanted complexity, size, and cost to the diagnostic equipment.

As a result, performing signal filtering with portable diagnostic equipment to remove artifacts while recovering the signal of interest presents several challenges.

SUMMARY

The present application describes techniques to adaptively filter signals having mixed blunt noise, which may be characterized as noise having relatively high amplitudes and low frequencies having a frequency spectrum that overlaps with that of the signal of interest. Filtering may be accomplished implementing an Epsilon-tube ($\varepsilon$-tube) filter.

The adaptive filter may function to filter signals within a series of successively received sliding-time windows such that signals may be sampled and filtered in real-time or near real-time. The signal may be received in accordance with any suitable type of diagnostic, preventative, or other test. For example, the signals may be received in accordance with testing utilizing electrocardiogram, impedance cardiographs, impedance-based blood volume waveforms, arterial blood pressure waveform, venous blood pressure waveforms, intracranial pressure waveforms, photoplethysmography waveforms, end-tidal carbon dioxide waveforms, light absorption spectral signals, Doppler signals, piezoelectric signals, etc.

Accordingly, the signal may include one or more primary signal components having relatively constant amplitudes (e.g., less than a 10% change) over short periods of time, such as the time period corresponding to one or more sliding time windows, for example, which is further discussed below. The signal amplitudes may vary slowly over time, but may remain relatively constant within a single sliding time window (e.g., a window of 5 seconds, 10 seconds, etc.). Embodiments include filtering the signal by adapting one or more filter coefficients over time to account for changes in the structure of the signal and/or the introduction of blunt noise that may contaminate the signal at some periods of time (e.g., when a patient is moving) but not others (e.g., when a patient is still).

Within each of the sliding-time windows, the blunt noise may be estimated using a plurality of movement signals, which may be received from one or more respective accelerometer and/or gyroscope sensors, for example. The signal may be sampled within each of the plurality of successive sliding time windows together with the plurality of movement signals. Upon calculation and application of a set of filter coefficients, the plurality of movement signals may be utilized such that a blunt noise model estimation of the blunt noise is subtracted from the signal to retain the primary component of the signal. The process of calculating sets of filter coefficients may be repeated over several successive sliding time windows, thereby facilitating real-time (or near real-time, with some slight processing delay) signal filtering with a portable device.

To prevent the calculated set of filter coefficients from filtering out the primary component of the signal (e.g., a respiratory component of an impedance plethysmography signal) separate conditions may be implemented that guide the calculation of the sets of filter coefficients for each of the plurality of successive sliding time windows.

First, the filtered signal amplitude within a sliding time window may be limited or "clamped" between a threshold value that is based upon the amplitude of the primary signal component. In some embodiments, this threshold value, or margin, may be the same value as the primary component signal amplitude, forming a "tube," or more specifically an "Epsilon tube," around the primary component of the signal. In other embodiments, the threshold value may deviate from the primary component signal amplitude.

Furthermore, embodiments include one or more processors adapting the threshold value as each of the plurality of successive sliding windows are filtered such that the threshold value is adapted to the signal over time. For example, the threshold value may be adjusted when the threshold value was exceeded by the amplitude of the primary component of the signal within a previously received sliding window compared to the sliding time window in which the signal is being currently processed.

In an embodiment, one or more processors of the portable device may adjust the threshold value, calculate the set of filter coefficients, calculate the prototype signal, and/or filter the signal when the blunt noise is present in the signal. The presence or absence of blunt noise within the signal may be determined, for example, based upon a power level of one or more of the plurality of movement signals exceeding a respective threshold power level.

In an embodiment, regardless of when the threshold value is adjusted, the threshold value may be adjusted by one or more processors of the portable device to a new threshold value that is proportional to an amount in which the threshold value was exceeded by the amplitude of the primary component in the previous sliding time window.

Second, to facilitate the extraction of the primary components of the signal, one or more processors of the portable device may calculate a prototype signal that models dominant frequency components of the signal from one or more sliding time windows that chronologically precede the sliding time window in which the signal is being currently processed. Using an example of an impedance plethysmography signal, the dominant frequency component may correspond to, for example, the respiratory frequency component, which advantageously tends to be fairly periodic. The set of filter coefficients may be calculated to satisfy another condition to minimize the error between frequency components of the filtered signal within the sliding time window being currently processed and the frequency components of the prototype signal.

In an embodiment, the prototype signal may be calculated by one or more processors of the portable device by calculating a minimized error between frequency components of the filtered signal within a sliding window and the calculated prototype signal based upon a Stockwell transform or other suitable frequency transform algorithm (e.g., a Fourier transform, a short time Fourier transform, a Gabor transform, etc.). Moreover, the prototype signal may be calculated via a piecewise linear approximation of the square of the magnitude of the frequency components of the signal after transformation within one or more of the preceding sliding time windows.

BRIEF DESCRIPTION OF THE DRAWINGS

The Figures described below depict various aspects of the system and methods disclosed herein. It should be understood that each figure depicts an aspect of a particular aspect of the disclosed system and methods, and that each of the Figures is intended to accord with a possible aspect thereof. Further, wherever possible, the following description refers to the reference numerals included in the following Figures, in which features depicted in multiple Figures are designated with consistent reference numerals.

There are shown in the Figures arrangements which are presently discussed, it being understood, however, that the present embodiments are not limited to the precise arrangements and instrumentalities shown, wherein.

Figure 1:
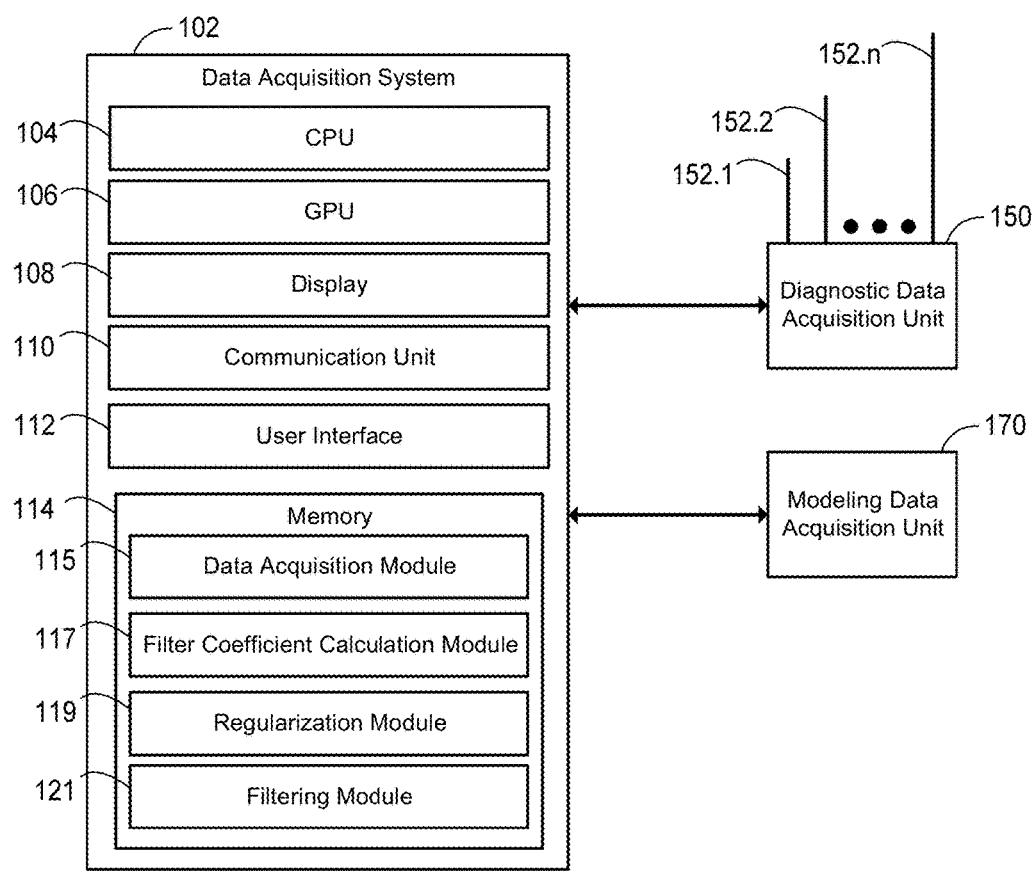
FIG. 1 illustrates a block diagram of an exemplary system 100 in accordance with an exemplary aspect of the present disclosure.

The Figures depict preferred embodiments for purposes of illustration only. Alternative embodiments of the systems and methods illustrated herein may be employed without departing from the principles of the invention described herein.

DETAILED DESCRIPTION

The present application describes various embodiments in the context of techniques using diagnostic systems to generate, measure, receive, sample, analyze, process, and/or filter one or more diagnostic signals. These diagnostic systems may include those used to non-invasively or invasively monitor one or more biological processes for a patient undergoing a test procedure. For example, diagnostic systems may be used to monitor changes in the volume of blood in the venous system of patients. Such techniques may utilize an impedance plethysmography (IP) system as one example, but may also include any suitable type of diagnostic system such as photoplethysmography, electromyography, ultrasound, etc.

Furthermore, the embodiments described herein are applicable to any suitable type of system having periodic signals with slowly varying amplitudes that may be prone to noise contamination. In various embodiments, this may include medical or non-medical diagnostic systems. For example, the filtering methods described herein may be applied to medical diagnostic systems configured to generate, measure, receive, sample, analyze, process, and/or filter signals associated with electrocardiograms, impedance cardiography, impedance plethysmography, arterial blood pressure waveforms, venous blood pressure waveforms, intracranial pressure waveforms, photoplethysmography waveforms, end-tidal carbon dioxide waveforms, Doppler signals, piezoelectric signals, etc.

To provide additional examples, the filtering methods described herein may also be applied to non-medical diagnostic systems configured to generate, measure, receive, sample, analyze, process, and/or filter signals associated with exercise equipment, biometric sensors, fitness trackers, wearable electronic devices, and other physiological and/or behavioral measurement devices.

Impedance Plethysmography and Respiratory Rate

The various embodiments explained herein often refer to impedance plethysmography (IP) signals as illustrative examples, but these embodiments are equally applicable to any suitable type of periodic signals that may be adequately sampled and filtered in accordance with the techniques presented herein, e.g., signals indicating physiological conditions of a person or subject, and/or signals indicating behavioral conditions of the same. A brief explanation of impedance plethysmographs is presented below for clarity.

Conventionally, impedance plethysmographs may be used to determine changes in blood volume and oxygenation within portions of a patient's limb, which is particularly useful in diagnosing conditions such as venous thrombosis. Impedance plethysmographs typically function by injecting a high-frequency, low amplitude sinusoidal current into a segment of interest using a pair of skin electrodes, or current electrodes. Another pair of electrodes is also used to measure an imposed voltage difference between the current injection points, which is caused by the passage of electrical current through the patient's tissue. A diagnostic signal, in this case an IP signal, may then be generated based upon a ratio between the measured voltage and the injected current. Because the electrical conductivity of the tissue is mainly influenced by the volume of blood in that region, variations of the measured voltage (and thus variations in the impedance) cause the IP signal to reflect variations caused by the blood's electrical conductivity in the segment of interest due to changes in blood volume.

One of the main sources of blood volume variation and tissue movement, in particular in the chest and abdomen area, is respiration. As a result, the respiratory signal and the respiratory rate may be extracted from an IP signal acquired from the thorax and abdomen area when the subject is motionless. However, a patient's movement is also a large source of blood volume variation. Moreover, the electrodes and/or the skin can slide over the tissue due to the patient's movements. As a result, a patient's movement during an administered IP test may result in drastic variations in the measured IP signal resulting in blunt noise. In such a case, "motion artifacts" may occur having amplitudes larger than the amplitude of the respiratory component of the IP signal and a frequency spectrum that overlaps with the range of normal respiratory rates. As a result, it is desirable to use filtering methods to eliminate the MA's before the signal is used for monitoring respiration.

FIG. 1 illustrates a block diagram of an exemplary system 100 in accordance with an exemplary aspect of the present disclosure. System 100 may include a data acquisition system 102, a diagnostic data acquisition unit 150, n number of electrodes 152.1-152.n, and a modeling data acquisition unit 170. In an embodiment, system 100 may be implemented as a closed loop system.

Diagnostic data acquisition unit 150 may be implemented as any suitable type of diagnostic device configured to receive signals via electrodes 152.1-152.n. Depending on the particular type of test that is performed, diagnostic data acquisition unit 150 may be implemented as one or more types of diagnostic devices. Diagnostic data acquisition unit 150 may be configured to receive signals via electrodes 152.1-152.n, to process these signals, and/or to send the signals received via electrodes 152.1-152.n and/or the processed signals to data acquisition system 102.

Electrodes 152.1-152.n may be configured as any suitable type of device to measure, monitor, and/or generate electrical signals based upon their location on a test subject and/or the type of test being performed via diagnostic data acquisition unit 150. For example, if diagnostic data acquisition unit 150 is implemented as an electrobioimpedance amplifier, then electrodes 152.1-152.n may be configured in accordance with a system that is compatible with such a system. To provide another example, if diagnostic data acquisition unit 150 is used to conduct an IP test, some of electrodes 152.1-152.n may be configured as current injecting electrodes while some of electrodes 152.1-152.n may be configured as voltage monitoring electrodes. Thus, electrodes 152.1-152.n may provide diagnostic data acquisition unit 150 with the appropriate signals to generate one or more IP signals and/or to send the IP signals to data acquisition system 102.

Electrodes 152.1-152.n may be placed in any suitable location to provide signals in accordance with the type of application and/or the test being conducted. For example, if an electrocardiography (ECG) measurement is performed, one or more of electrodes 152.1-152.n may be placed on a suitable portion of a patient's chest. To provide another example, if an IP test is performed, one or more of electrodes 152.1-152.n may be placed on a suitable portion of the patient commensurate with an IP test, such as between the patient's third and tenth ribs, a traditional trans-thoracic electrode placement, etc.

Modeling data acquisition unit 170 may be configured to measure, generate, receive, and/or monitor one or more data signals associated with the source of noise introduced into the diagnostic signal measured by diagnostic data acquisition unit 150. In some specific examples, that diagnostic signal contains physiological data and/or behavioral data on a patient or other subject. Modeling data acquisition unit 170 may be implemented as any number and/or type of sensors based upon the source of the noise introduced into the diagnostic signal that is to be modeled.

In an embodiment, the noise may include, for example, blunt noise. In embodiments in which the blunt noise takes the form of MAs, modeling data acquisition unit 170 may be implemented as one or more sensors configured to monitor the patient's movement. Some examples of these types of sensors may include accelerometers, gyroscopes, pressure sensors, piezoelectric sensors, etc. To provide an illustrative example, modeling data acquisition unit 170 may be implemented as a three-axis accelerometer configured to measure acceleration in the x, y, and z-axes. Modeling data acquisition unit 170 may be worn by and/or attached to a patient such that these accelerometer signals represent one or more movement signals indicative of the patient's movement in each of the x, y, and z-axes. Modeling data acquisition unit 170 may be configured to transmit the acceleration signals and/or one or more movement signals to data acquisition system 102.

Data acquisition system 102 may include a central processing unit (CPU) 104, a graphics processing unit (GPU) 106, a display 108, a communication unit 110, a user interface 112, and a memory 114. In various embodiments, data acquisition system 102 may be implemented as any suitable computing device, which may include a portable or stationary computing device such as a smartphone, a mobile device, a tablet computer, a laptop computer, a dedicated diagnostic system, a personal computer, a wearable computing device, etc.

In some embodiments, data acquisition system 102 may be implemented as a single device, for example, as shown in FIG. 1. Such implementations may be particularly useful when a portable and/or mobile device is desirable. In other embodiments, data acquisition system 102 may be implemented as a device that may perform functions of two or more devices, such as a device that may perform functions of one or more of data acquisition system 102, diagnostic data acquisition unit 150, and/or modeling data acquisition unit 170, for example. Such implementations may be particularly useful when it is desirable to modify an existing off-the-shelf system to perform the embodiments as described herein, for example, by performing a software and/or firmware upgrade, by adding specialized hardware cards or modules, etc.

Display 108 may be implemented as any suitable type of display and may facilitate user interaction in conjunction with user interface 112, such as a mobile device display, a smartphone display, a capacitive touch screen display, a resistive touch screen display, etc. In various aspects, display 108 may be configured to work in conjunction with CPU 104 and/or GPU 106 to display one or more diagnostic signals received and processed by communication unit 110 and/or filtered by CPU 104 executing instructions in one or more modules stored in memory 114.

Communication unit 110 may be configured to process, send signals to, and/or receive signals from diagnostic data acquisition unit 150 and/or modeling data acquisition unit 170. Communication unit 110 may be configured to communicate with diagnostic data acquisition unit 150 and/or modeling data acquisition unit 170 in accordance with any suitable type and/or number of wired and/or wireless communication protocols.

User interface 112 may be configured to receive user-input and to facilitate user interaction with data acquisition system 102. For example, user-interface 112 may be implemented as a "soft" keyboard that is displayed on display 108, an external hardware keyboard communicating via a wired or a wireless connection (e.g., a Bluetooth keyboard), an external mouse, or any other suitable user-input device.

User-interface 112 may include a microphone configured to receive user input in the form of voice input, such as voice commands, for example. In some aspects, voice commands received via user interface 112 may be converted to text, for example, via CPU 104. In this way, user interface device 112 may allow a user to enter text in lieu of typing. User interface 112 may facilitate a user adjusting, modifying, changing, etc., one or more options or settings of data acquisition system 102 depending on a particular implementation. For example, a user may utilize user interface 112 to change display settings, to change one or more design parameters used in the signal filtering process as further discussed below, etc.

CPU 104 and/or GPU 106 may be configured to communicate with memory 114 to store to and read data from memory 114. In accordance with various embodiments, memory 114 may be a computer-readable non-transitory storage device that may be implemented as any suitable combination of volatile (e.g., a random access memory (RAM), and/or non-volatile memory (e.g., battery-backed RAM, FLASH, etc.). Memory 114 may be configured to store instructions executable on CPU 104 and/or GPU 106. These instructions may include machine-readable instructions that, when executed by CPU 104 and/or GPU 106, cause CPU 104 and/or GPU 106 to perform various acts.

Data acquisition module 115, filter coefficient calculation module 117, regularization module 119, and filtering module 121 are portions of memory 114 configured to store instructions executable by CPU 104 and/or GPU 106. In accordance with various embodiments, any of data acquisition module 115, filter coefficient calculation module 117, regularization module 119, and/or filtering module 121 may operate as a separately executable software application, a plugin that extends the functionality of another software application such as a web browser, an application programming interface (API) invokable by a software application, etc. The instructions included within any of any of data acquisition module 115, filter coefficient calculation module 117, regularization module 119, and/or filtering module 121 may be compiled and executable on CPU 104 and/or GPU 106 directly, or not compiled and interpreted by the CPU 104 and/or GPU 106 on a runtime basis.

Data acquisition module 115 may include instructions that, when executed by CPU 104 and/or GPU 106, causes CPU 104 and/or GPU 106 to receive, sample, store, and/or process data received from diagnostic data acquisition unit 150 and/or modeling data acquisition unit 170 via communication unit 110. In various embodiments, this data may include, for example, sampled data representative of signals received from diagnostic data acquisition unit 150 over one or more sliding time windows, data representative of signals received from modeling data acquisition unit 170 over one or more sliding time windows, etc.

Filter coefficient calculation module 117 may include instructions that, when executed by CPU 104 and/or GPU 106, causes CPU 104 and/or GPU 106 to retrieve data stored by data acquisition module 115 and to utilize this data to calculate a set of filter coefficients with respect to one or more sliding time windows, which may be successively received via communication unit 110, for example, via diagnostic data acquisition unit 150 and/or modeling data acquisition unit 170.

In various embodiments, filter coefficient calculation module 117 may include instructions to facilitate the modeling of blunt noise using the sampled data measured by modeling data acquisition unit 170, which may be indicative of the source of the blunt noise. In embodiments in which the blunt noise is caused by a patient's movement, modeling module 117 may include instructions to construct models using one or more movement signals, which may include one or more accelerometer signal values. The techniques represented by the instructions to construct models are further discussed in detail below.

As will be discussed in further detail, filter coefficient calculation module 117 may include instructions to facilitate the calculation of a set of filter coefficients using an optimized objective function and/or the satisfaction of one or more constraints such that any suitable number of conditions are satisfied. One such condition may be satisfied when the diagnostic signal amplitude within a sliding time window is limited by a threshold value.

That is, the filtered signal amplitude within a sliding time window may be limited, or "clamped" between a threshold value that is based upon the primary signal component amplitude within the same sliding time window. In some embodiments, this threshold value, or margin, may be the same value as the primary component signal amplitude, forming a "tube," or more specifically "ε-tube," around the signal. In other embodiments, the threshold value may deviate from the primary component signal amplitude.

To filter a signal contaminated with blunt noise, the original contaminated signal may be filtered according to one or more sets of filter coefficients such that the blunt noise model is subtracted from the original signal to produce a filtered signal. Thus, to avoid distortion of the filtered signal, an ε-tube value or other suitable threshold value may be used to constrain the calculated filter coefficients to those solutions that provide filtered signal amplitudes having amplitudes less than the amplitude of the primary component of the original contaminated signal for a respective sliding time window in which a sampled signal is being processed. In this way, filter coefficient calculation module 117 includes instructions to facilitate the calculation of sets of filter coefficient solutions by CPU 104 and/or GPU 106 that produce filtered signals having amplitudes that are "clamped" by the ε-tube or other threshold value. Because several sets of filter coefficients may satisfy this constraint, additional calculations, which are further discussed below, may be used to find the filter coefficient solution.

Furthermore, embodiments include filter coefficient calculation module 117 facilitating CPU 104 and/or GPU 106 adapting or adjusting ε-tube or other threshold value as each of the plurality of successive sliding windows are filtered such that the ε-tube or other threshold value is adapted to the signal as the signal is sampled over several sliding time windows. For example, the threshold value may be adjusted when the threshold value was exceeded by the amplitude of the filtered signal.

In an embodiment, filter coefficient calculation module 117 may facilitate CPU 104 and/or GPU 106 adjusting the ε-tube or other threshold value and/or calculating the set of filter coefficients when the blunt noise is present in the signal. The presence or absence of blunt noise within the signal may be determined, for example, based upon a power level of one or more of the plurality of movement signals exceeding a respective threshold power level, which may be determined, for example, via instructions stored in data acquisition module 115 being executed by CPU 104 and/or GPU 106.

In an embodiment, regardless of when the ε-tube or other threshold value is adjusted, the ε-tube or other threshold value may be adjusted by CPU 104 and/or GPU 106 to a new threshold value that is proportional to an amount in which the ε-tube or other threshold value was exceeded by the amplitude of the primary signal component in a sliding time window that chronologically preceded the sliding time window in which a sampled signal is being currently processed.

Regularization module 119 may include instructions that, when executed by CPU 104 and/or GPU 106, causes CPU 104 and/or GPU 106 to select a set of filter coefficients that satisfy the ε-tube constraint as well as one or more additional conditions. For example, CPU 104 and/or GPU 106 may select a set of filter coefficients that satisfy the ε-tube constraint and minimize an objective function.

Further continuing this example, to minimize the objective function, the instructions stored in regularization module 119 may facilitate CPU 104 and/or GPU 106 calculating a prototype signal that models dominant frequency components of the signal from a second sliding time window that chronologically precedes the first sliding time window. The prototype signal may be calculated, for example, via a piecewise linear approximation of the square of the magnitude of the frequency components of the signal within the second sliding time window.

In an embodiment, instructions stored in regularization module 119 may facilitate CPU 104 and/or GPU 106 to select a set of filter coefficients that minimize the error between frequency components of the filtered signal within the sliding time window and the frequency components of the calculated prototype signal. The prototype may be calculated, for example, through the use of a Stockwell transform or any suitable type of frequency transform algorithm (e.g., a Fourier transform, a short time Fourier transform, a Gabor transform, etc.), to calculate the relevant frequency components.

In an embodiment, regularization module 119 may facilitate CPU 104 and/or GPU 106 to calculate the prototype signal when the blunt noise is not present in the signal. Again, the presence or absence of blunt noise within the signal may be determined, for example, based upon a power level of one or more of the plurality of movement signals exceeding a respective threshold power level.

Filtering module 121 may include instructions that, when executed by CPU 104 and/or GPU 106, causes CPU 104 and/or GPU 106 to store and/or process data used in conjunction with the overall filtering process implemented by data acquisition system 102 in accordance with the embodiments as described herein. For example, filtering module 121 may store, as part of its instructions, data such as defined filter design variables, sliding time window scales, processing windows and/or sliding time windows, design constraints, one or more filter parameters, user selections, filter coefficients, ε-tube values, threshold values, and/or predetermined constants used by data acquisition system 102 to filter diagnostic signals.

To provide another example, filtering module 121 may include instructions that, when executed by CPU 104 and/or GPU 106, causes CPU 104 and/or GPU 106 to apply the filter coefficient solutions to the diagnostic signals to facilitate real-time (or near real-time due to slight processing delays) diagnostic signal filtering.

In various embodiments, one or more of data acquisition module 115, filter coefficient calculation module 117, regularization module 119, and/or filtering module 121 may include instructions that cause CPU 104 and/or GPU 106 to work in conjunction with user interface 112, for example, to receive data used in conjunction with the overall filtering process. In this way, a user may originally program the instructions stored in one or more of data acquisition module 115, filter coefficient calculation module 117, regularization module 119, and/or filtering module 121, for example, and later overwrite these instructions to update the data.

In other embodiments, one or more of data acquisition module 115, filter coefficient calculation module 117, regularization module 119, and/or filtering module 121 may include instructions that cause CPU 104 and/or GPU 106 to work in conjunction with communication unit 110, for example, to set one or more data values used in the filtering process, such as the £ value, one or more threshold values, and/or prototype signal, based upon characteristics of the measured signal such as signal amplitude, frequency components, etc.

In an embodiment, filtering module 121 may facilitate CPU 104 and/or GPU 106 filtering the signal only when the blunt noise is present in the signal. Again, the presence or absence of blunt noise within the signal may be determined, for example, based upon a power level of one or more of the plurality of movement signals exceeding a respective threshold power level.

In various embodiments, the filtered signals received from the patient may assist a physician or other medical personnel in diagnosing and/or treating one or more patient conditions. In accordance with such embodiments, treatments may be administered in any suitable manner. For example, a physician may manually administer and/or treat a patient using the filtered signal information. To provide another example, one or more diagnostic and/or therapeutic devices may be configured to administer treatments to a patient based upon the filtered signal information in accordance with a default and/or preconfigured treatment process, which may include automatic treatments not requiring human intervention. Devices configured to perform treatment processes based upon the filtered signal information are not shown in FIG. 1 for purposes of brevity. However, embodiments may include, for example, one or more treatment administration apparatuses having a respective treatment control device configured to, upon receiving data indicating a sufficient condition of the patient based upon the filtered signal information, instruct the therapeutic delivery vehicle to administer a therapeutic treatment to the patient, hopefully to fully address the subject's condition.

Figure 2:
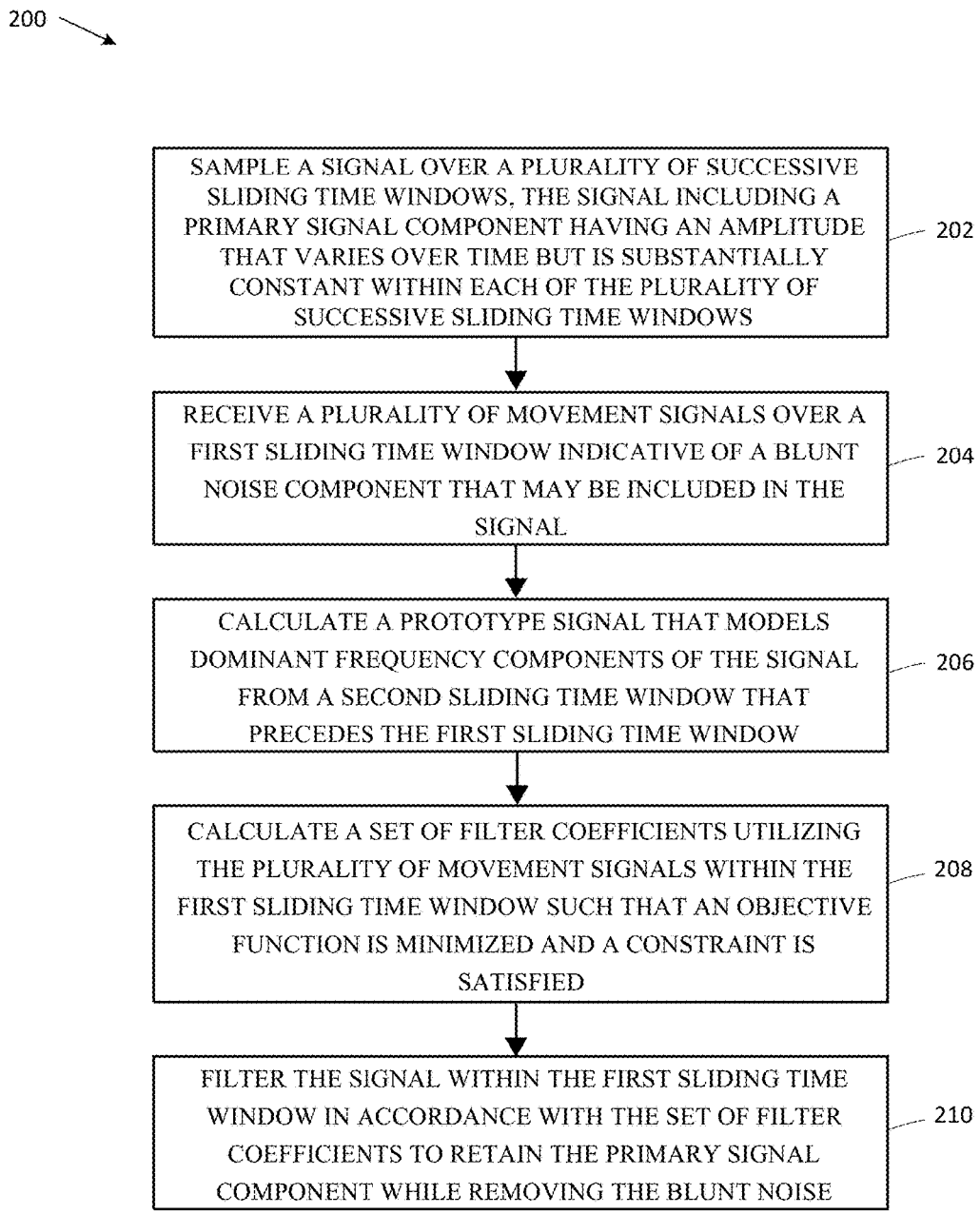
FIG. 2 illustrates an example method 200 in accordance with an exemplary aspect of the present disclosure.

FIG. 2 illustrates an example method 200 in accordance with an exemplary aspect of the present disclosure. In an embodiment, method 200 may be implemented by any suitable computing device, such as data acquisition system 102, for example, as shown in FIG. 1. In an embodiment, method 200 may be performed by one or more processors executing one or more algorithms, applications, programs, and/or routines, such as any suitable portion of CPU 104 and/or GPU 106 executing instructions stored in one or more of data acquisition module 115, modeling module 117, regularization module 119, and/or filtering module 121, for example, as shown in FIG. 1.

Method 200 may start when one or more processors sample a signal over one or more of a plurality of successive sliding time windows, the signal including a primary signal component having an amplitude that has a relatively constant amplitude (block 202). This signal may be sampled, for example, via communication unit 110 of diagnostic data acquisition unit 150, as shown in FIG. 1 (block 202). In an embodiment, the signal may include a primary signal component and blunt noise. The primary signal component may have a signal amplitude that varies over time but is substantially constant within the processing window. The signal may correspond to any suitable type of signal that may be prone to blunt noise contamination, such as an IP signal, a periodic diagnostic medical signal having a primary component, etc. In the case of an IP signal, this primary component may correspond to the respiratory component of the IP signal.

Method 200 may include one or more processors receiving a plurality of movement signals over a first sliding time window from among the plurality of successive sliding time windows, the plurality of movement signals being indicative of a blunt noise component that may be included in the signal within the first sliding time window (block 204). The movement signals may be received, for example, via communication unit 110 of modeling data acquisition unit 170, as shown in FIG. 1 (block 204). The movement signals may represent, for example, accelerometer data indicative of a patient's movement causing the blunt noise to be introduced into the sampled signal (block 202).

Method 200 may include one or more processors calculating a prototype signal that models dominant frequency components of the signal from a second sliding time window that chronologically precedes the first sliding time window (block 206). To provide another example, the prototype signal may be calculated via a piecewise linear approximation of the square of the magnitude of the frequency components of the signal within the second sliding time window (block 206). Method 200 may include, for example, one or more processors calculating the filter coefficients by calculating an error between frequency components of the filtered signal within the first sliding time window and the prototype signal based upon a Stockwell transform or other suitable frequency transform algorithm (e.g., a Fourier transform, a short time Fourier transform, a Gabor transform, etc.) (block 206).

Method 200 may include one or more processors calculating a set of filter coefficients utilizing the plurality of movement signals within the first sliding time window such that one or more conditions are satisfied, which may include the satisfaction of one or more constraints and/or the optimization of one or more objective functions, for example (block 208). A constraint may be satisfied, for example, when the filtered signal amplitude within the first sliding time window is limited between a threshold value based upon the primary signal component amplitude within the same sliding time window (block 208). An objective function may be minimized, for example, when the error between frequency components of the filtered signal within the first sliding time window and the frequency components of the prototype signal is minimized (block 208).

Method 200 may include one or more processors filtering the signal within the first sliding time window in accordance with the set of filter coefficients to retain the primary signal component while removing the blunt noise (block 210).

The following pages further explain the adaptive filtering process in accordance with various embodiments of the disclosure. Unless specifically noted, one or more of the following processes, which may include the incorporation of mathematical equations, may be implemented by one or more portions of system 100, as shown in FIG. 1.

Figure 3:
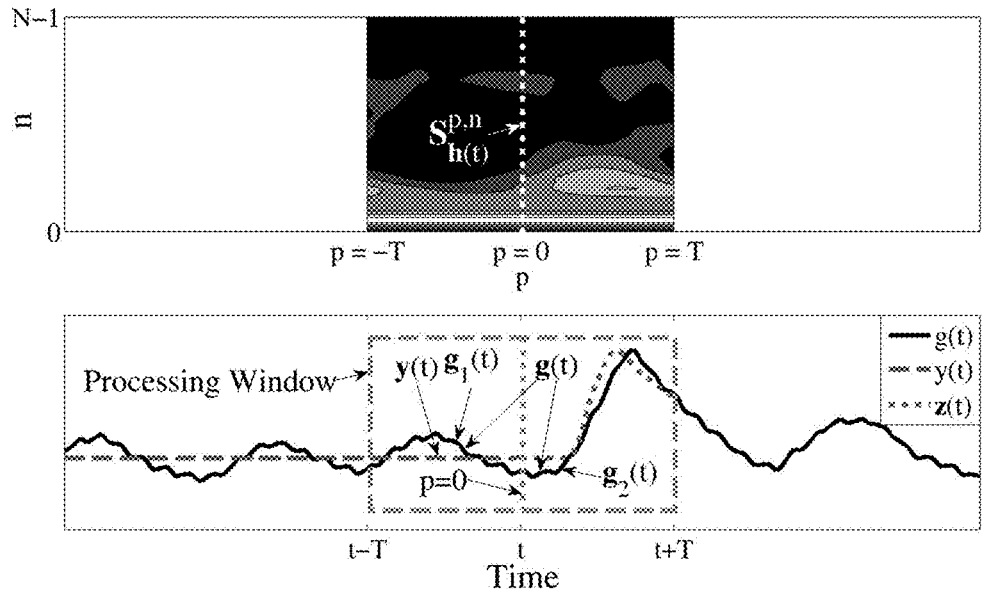
FIG. 3 illustrates a sliding processing window over a signal that has been corrupted by noise and a Stockwell transform (ST) of h(t) inside the processing window in accordance with an exemplary aspect of the present disclosure.

In an embodiment, the adaptive ε-tube filter may operate by sliding a processing window over a signal that has been corrupted by noise, as shown in FIG. 3. The bottom part shows a window from t−T to t+T, where t is the time index and 2T is the length of the processing window. The adaptive ε-tube filter may compute the filter coefficients at time t; therefore, the filter has a delay equal to T (typically equal to about half of the period for the diagnostic component of signal, e.g., around 5 seconds for an IP signal.)

Figure 4:
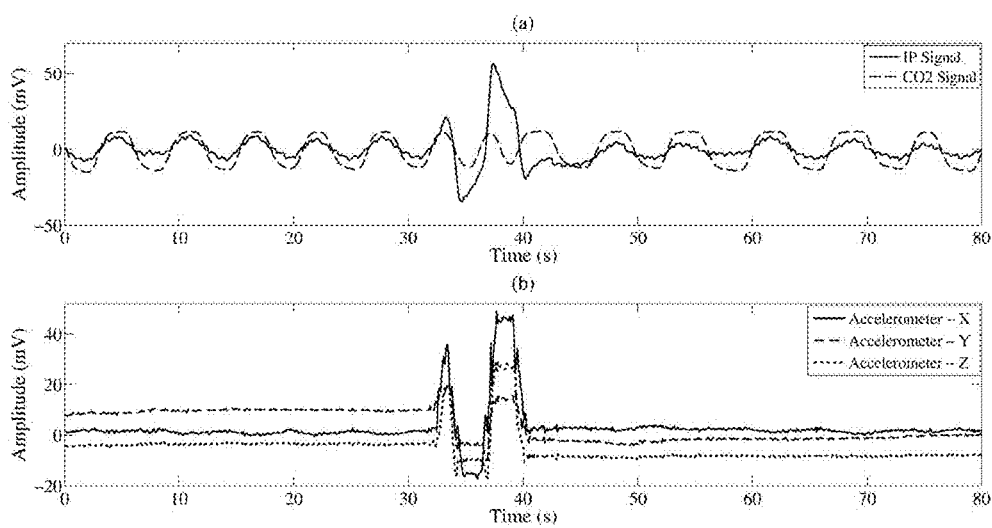
FIG. 4 illustrates diagnostic signals and movement signals in accordance with an exemplary aspect of the present disclosure.

The unfiltered signal value at time t is denoted by g(t) and the vector g(t) is used to signify the portion of the signal inside the processing window. The portion of the signal inside the processing window before t (from t−T to t−1) is denoted by $g_1(t)$ while the portion after t (from t to t+T) is denoted by $g_2(t)$. The filter output values y(t) have already been computed for all the signal samples preceding t and treated as constants when computing the filter coefficients at time t. The signal output values y(t) for the samples within the tube (from t−T to t−1) form vector y(t). In one embodiment, the blunt noise in the second half of the window (from t to t+T) may be estimated by:

$$z(t) = w^T(t)u(t)$$

where z(t) is the estimation for blunt noise at time t, w(t) is the vector of filter coefficients at time t and u(t) is the vector of filter inputs at time t (e.g. the movement signals measured via an accelerometer and/or gyroscope sensor, as shown in FIG. 4.) In another embodiment, an autoregressive element can be added to the equation above to model the exponential decaying effect that movements can induce into the corrupted signal. Assuming the above equation is utilized, the vector of the estimated blunt noise in the second half of the window, denoted by z(t), can be calculated using:

$$z(t) = U(t)w(t)$$

where U(t) is the matrix which contains the filter input values in the second half of the processing window from (t to t+T), i.e., the $i^{th}$ row in U(t) is u(t+i−1). After finding the best filter coefficients, w, to estimate the blunt noise in the second half of the processing window, the filter output at t is computed using:

$$y(t) = w^T(t)u(t)$$

and the processing window advances to the next signal sample at t+1 (from t−T+1 to t+T+1).

The filtered signal inside the processing window, denoted by h(t), can be found by augmenting y(t) with z(t) and subtracting it from g(t) In other words, $$h(t) = g(t) - \begin{pmatrix} y(t) \\ z(t) \end{pmatrix}$$
$$= \begin{pmatrix} g_1(t) \\ g_2(t) \end{pmatrix} - \begin{pmatrix} y(t) \\ z(t) \end{pmatrix}$$
$$= \begin{pmatrix} g_1(t) - y(t) \\ g_2(t) \end{pmatrix} - \begin{pmatrix} 0_{T \times 1} \\ z(t) \end{pmatrix}$$
$$= h_1(t) - h_2(t)$$

where $$h_1(t) = \begin{pmatrix} g_1(t) - y(t) \\ g_2(t) \end{pmatrix}, h_2(t) = \begin{pmatrix} 0_{T \times 1} \\ z(t) \end{pmatrix}$$

The top part of FIG. 3 shows the Stockwell transform (ST) of h(t) inside the processing window, denoted by $S_{h(t)}^{p,n}$, where p is the time index and n is the frequency index for the ST. The frequency decomposition of h(t) at p=0, denoted by $S_{h(t)}^{0,\cdot}$, can be found as:

$$S_{h(t)}^{0,\cdot} = S_{h_1(t)}^{0,\cdot} - S_{h_2(t)}^{0,\cdot}$$

The second term in the right side of the equation above can be expressed as a linear combination of STs of a shifted delta function, where the weights are the values in vector z(t), i.e., $$S_{h_2(t)}^{0,\cdot} = \sum_{k=0}^{T} z_k(t) S_{\delta(x-k)}^{0,\cdot} = M_\delta z(t)$$

where $M_\delta$ is a matrix whose $i^{th}$ column is $S_{\delta(x-i+1)}^{0,\cdot}$ where x∈[−T+1, T] is the argument of the delta function. Therefore, $$y(t) = z_0(t) = w^T(t)u(t).$$

The adaptive ε-tube filter may utilize a frequency prototype, denoted by r, that is calculated from previous processing windows to find the filter coefficients. In particular, the adaptive ε-tube filter may minimize the following objective function:

$$\text{Minimize}(r - S_h^{0,\cdot})^T \overline{(r - S_h^{0,\cdot})} + \frac{\gamma}{q} w^T w$$

where γ is design parameter that controls the balance between the two terms in the objective function and q is a non-negative non-decreasing function that represents the amount of noise in the signal. For example, in the case of the presence of a motion artifact, q can be calculated as the power of the movement signals or the power of the deviations of the noisy signal from the tube within the processing window. The latter case can be expressed as:

$$q(t) = \left[\frac{1}{2T} \sum_{i=t-T+1}^{t+T} e(i)^2\right]^{1/2}$$

where e(t)=max(g(t)−ε(t),−g(t)−ε(t),0). The process of finding r(t) and ε(t) will be explained later. The second term in the objective function $$\left(\frac{\gamma}{q} w^T w\right)$$

prevents the amplitude of the filter coefficients from growing excessively.

When q is sufficiently small (i.e., the subject is not moving and the movement signals have relatively low power levels), this second term becomes dominant and drives the amplitude of the filter coefficients towards zero. As a result, the adaptive ε-tube filter avoids modeling and manipulating the signal when there is no noise present in the signal. The objective function is convex and has a unique solution that can be found as:

$$w_{opt}(t) = -\left(U^T(t)C_2 U(t) + \frac{\gamma}{q(t)}I\right)^{-1} U^T(t)\text{Re}\left[C_1\left(r(t) - S_{h_1(t)}^{0,\cdot}\right)\right],$$

when q(t)>0 and $w_{opt}$=0 otherwise. Note that $C_1 = M_\delta^H$ and $C_2 = M_\delta^T \overline{M_\delta}$ A are constant matrices. Therefore, the update vector can be calculated using:

$$w_\Delta(t) = w_{opt}(t) - w(t-1).$$

Again, in an embodiment, one of the assumptions made by adaptive ε-tube filter is that the amplitude of the diagnostic component of the signal is relatively constant within each processing window. Hence, the filter may ensure that the amplitude of the filtered signal remains within a margin called an ε-tube (or "tube") and denoted by ε(t). In one embodiment, the tube constraints may be applied to the values in the middle of the processing window, i.e., $$-u^T(t)w(t) + g(t) + \varepsilon(t) \geq 0,$$

$$u^T(t)w(t) - g(t) + \varepsilon(t) \geq 0.$$

The left-hand side of the above constraint can be expressed in matrix form as $$v = Aw - b$$

where $$A = \begin{pmatrix} -u^T(t) \\ u^T(t) \end{pmatrix}, b = \begin{pmatrix} -g(t) - \varepsilon(t) \\ g(t) - \varepsilon(t) \end{pmatrix}.$$

A modified version of Rosen's gradient projection method can be used to enforce the tube constraints. In an embodiment, it is first assumed that the term w(t−1) satisfies the tube constraints. In accordance with such an embodiment, a matrix N is first formed whose columns are the gradients of the active constrains at w(t−1) (i.e., gradients of the rows of v at w(t−1)) for which:

$$(A^{i,\cdot})^T w_\Delta(t) \leq 0, i=1,2$$

where $A^{i,\cdot}$ is the $i^{th}$ row of matrix A. A constraint is said to be "active" if it holds at equality. If no active constraint exists that satisfies the above constraint, then the update vector d would be the same as $w_A(t)$. Otherwise, the update vector can be found by:

$$d = (I - N(N^T N)^{-1} N^T) w_A(t).$$

The inverse in the above equation is a scalar one, since the two tube constraints are in parallel (i.e., they are not active at the same time), and hence, the size of $N^T N$ is at most $1 \times 1$. Vector d defines the direction in which the update should take place. The filter coefficient vector update can be expressed using:

$$w(t) = w(t-1) + \alpha d,$$

where $\alpha$ is the step length. The step length is preferably equal to 1 if a full step does not violate the constraints; otherwise, $\alpha$ should preferably be the largest value such that $\alpha d$ does not violate any constraints. Accordingly, the first step is to find the constraint that would impose a bound on $\alpha d$ by finding index i for which:

$$(A^{i,\cdot})^T d < 0, \quad i = 1, 2$$

The step length is the largest value smaller than or equal to 1 such that:

$$\alpha \leq \frac{-((A^{i,\cdot})^T w(t-1) - b_i)}{(A^{i,\cdot})^T d}$$

The steps that are mentioned above to update the filter coefficient hold only if the tube constraints are satisfied at $w(t-1)$. Therefore, embodiments include the filter coefficients being corrected if the tube constraints are violated using:

$$w(t-1) \leftarrow w(t-1) + d_c,$$

where $d_c$ is the correction vector. To have a correction with minimal disturbance, the correction vector should preferably be perpendicular to the boundary of the constraint that is violated. To do so, first the constraint should be found that is violated by checking $v_i < 0$, $i = 1, 2$. Then, the correction vector can be computed using:

$$d_c = -N(N^T N)^{-1} A^{i,\cdot}$$

where $A^{i,\cdot}$ is the $i^{th}$ row of matrix A. The correction step should be performed prior to computing $w_A(t)$.

Figure 5:
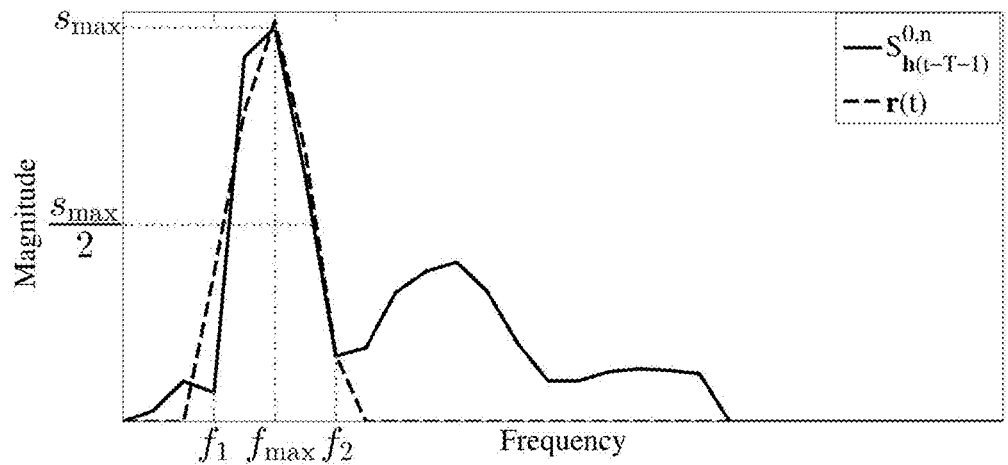
FIG. 5 illustrates a plot of the amplitudes of vectors r(t) and $S_{h(t-T-1)}^{0,n}$ in accordance with an exemplary aspect of the present disclosure.

The prototype r represents the frequency spectrum of the diagnostic component of the signal. It is assumed that this spectrum varies over time, but is relatively constant over short periods of time, such as the time period associated with a sliding time window, for example. In one embodiment, the prototype can be computed from a window that spans from $t-2T-1$ to $T-1$, as shown in FIG. 5, when the signal is clean and does not contain blunt noise. The ST of the signal in the middle of the window (at $p=0$) is shown with a solid line. The frequency that has the maximum amplitude is denoted by $f_{max}$. The first frequencies before and after $f_{max}$ whose amplitudes are smaller than or equal to half of the amplitude of $f_{max}$ are denoted by $f_1$ and $f_2$, respectively. Note that both $r(t)$ and $S_{h(t-T-1)}^{0,n}$ are complex valued vectors, but only their amplitudes are shown in FIG. 5.

We fit two linear models to the two segments in $S_{h(t-T-1)}^{0,n}$ from $f_1$ to $f_{max}$ and from $f_{max}$ to $f_2$. In an embodiment, this is realized by fitting linear models to the real and imaginary parts of $S_{h(t')}^{0,\cdot}$, $\text{Re}[S_{h(t')}^{0,\cdot}]$ and $\text{Im}[S_{h(t')}^{0,\cdot}]$ where $t' = t - T - 1$. Let us define:

$$y_{r1} = \begin{pmatrix} \text{Re}[S_{h(t')}^{0,f_1}]^2 \\ \text{Re}[S_{h(t')}^{0,f_1+1}]^2 \\ \vdots \\ \text{Re}[S_{h(t')}^{0,f_{max}}]^2 \end{pmatrix}, \quad y_{i1} = \begin{pmatrix} \text{Im}[S_{h(t')}^{0,f_1}]^2 \\ \text{Im}[S_{h(t')}^{0,f_1+1}]^2 \\ \vdots \\ \text{Im}[S_{h(t')}^{0,f_{max}}]^2 \end{pmatrix}$$

$$y_{r2} = \begin{pmatrix} \text{Re}[S_{h(t')}^{0,f_{max}}]^2 \\ \text{Re}[S_{h(t')}^{0,f_{max}+1}]^2 \\ \vdots \\ \text{Re}[S_{h(t')}^{0,f_2}]^2 \end{pmatrix}, \quad y_{i2} = \begin{pmatrix} \text{Im}[S_{h(t')}^{0,f_{max}}]^2 \\ \text{Im}[S_{h(t')}^{0,f_{max}+1}]^2 \\ \vdots \\ \text{Im}[S_{h(t')}^{0,f_2}]^2 \end{pmatrix}$$

$$X_1 = \begin{pmatrix} 1 & f_1 \\ 1 & f_1+1 \\ \vdots & \vdots \\ 1 & f_{max} \end{pmatrix}, \quad X_2 = \begin{pmatrix} 1 & f_{max} \\ 1 & f_{max}+1 \\ \vdots & \vdots \\ 1 & f_2 \end{pmatrix}$$

The least squares estimates for real and imaginary parts of the two aforementioned parts in $S_{h(t-T-1)}^{0,\cdot}$ can be computed using:

$$\hat{y}_{r1} = X_1 (X_1^T X_1)^{-1} X_1^T y_{r1},$$

$$\hat{y}_{i1} = X_1 (X_1^T X_1)^{-1} X_1^T y_{i1},$$

$$\hat{y}_{r2} = X_2 (X_2^T X_2)^{-1} X_2^T y_{r2},$$

$$\hat{y}_{i2} = X_2 (X_2^T X_2)^{-1} X_2^T y_{i2}.$$

The estimated real and imaginary parts can be incorporated as follows, $$l_1 = \sqrt{\max(\hat{y}_{r1}, 0)} + j\sqrt{\max(\hat{y}_{i1}, 0)},$$

$$l_2 = \sqrt{\max(\hat{y}_{r2}, 0)} + j\sqrt{\max(\hat{y}_{i2}, 0)},$$

where the square root and max are element-wise operators. The prototype can be found as $$r'(t) = [0_{1 \times (f_1-1)}, l_1'^T, \mu l_2'^T, 0_{1 \times (N-f_2)}]^T,$$

where $l_1'$ is the same as $l_1$ excluding the last element, $l_2'$ is the same as $l_2$ excluding the first element and $\mu$ is the mean of the last element of $l_1$ and the first element of $l_2$. As a result, $|r(t)|^2$ is a piecewise linear approximation for $|S_{h(t-T-1)}^{0,\cdot}|^2$ from $f_1$ to $f_2$. Finally, the adaptive $\epsilon$-tube filter adjusts the phase of the prototype to match that of $S_{h(t)}^{0,\cdot}$ as follows, $$r_n(t) = |r_n'(t)| \cdot e^{-\frac{j 2\pi n (\tau(n)-1)}{2T}}$$

where $r_n$ is the element of vector r that is associated with frequency n and $\tau(n)$ is the circular shift associated with frequency n that is calculated from the previous sliding time window as $$\tau(n) = -\frac{\phi(S_{h(t-1)}^{0,\cdot}) 2T}{2\pi n}.$$

The performance of the filter can be increased by shifting $S_{h(t-T-1)}^{0,\cdot}$ such that $f_{max} = 0$ and precompute $X_1 (X_1^T X_1)^{-1} X_1^T$ and $X_2 (X_2^T X_2)^{-1} X_2^T$ for different values of $f_1$ and $f_2$, which would eliminate the potentially time-consuming step of computing the inverse.

In one embodiment, the adaptive ε-tube filter may update the prototype based on $S_{h(t-T-1)}^{0,\cdot\cdot}$ only when the signal is in a calm state, as defined later. When there is blunt noise present in the signal, embodiments include the adaptive ε-tube filter utilizing the last prototype that was computed based on a window that was in a calm state. In this way, the filter may prevent the noise from entering the prototype, which can otherwise lead to propagation of error.

The prototype that is described above relies upon the diagnostic signal being periodic with one major frequency component. However, some physiological signals, such as electrocardiogram or piezoelectric signals, for example, may have a pattern that constitutes several frequency components. In one embodiment, the prototype may be modified to reflect the inherent characteristics of the diagnostic signal. In other embodiments, the signal may be low-pass filtered to remove most of the frequencies that are associated with the details of the signal and keep the frequencies that are associated with the main periodic component of the signal. Then, the adaptive ε-tube filter, along with the aforementioned prototype, may be used to estimate the motion artifact. The estimated motion artifact may be subtracted from the original signal to obtain a clean signal with the details.

In an embodiment, the adaptive ε-tube filter may impose a margin on the amplitude of the filtered signal. The size of the margin, ε(t), may vary gradually over time as the amplitude of the diagnostic component of the signal changes. As a result, the adaptive ε-tube filter may adaptively change the width of the tube, which may advantageously be done when the signal is in a calm state. In one embodiment, the power of the movement signals for a particular processing window may be used to determine whether or not the signal is in a calm state. The signal is said to be in a calm state when the power of the movement signals is smaller than a threshold value, which may be set to any suitable value.

In one embodiment, the filter decides whether the size of the tube needs to be decreased or increased if the signal is in a calm state. That is, if the portion of the signal inside the tube violates the tube, then the tube size may be increased by some suitable amount, which may be proportional to the tube size or the size of the violation (e.g., 1% of the size of the violation). Otherwise, the adaptive ε-tube filter may decide whether the size of the tube needs to be decreased or not, which may be determined by analyzing a suitably sized window (e.g., a window from t−4T to T).

Figure 6:
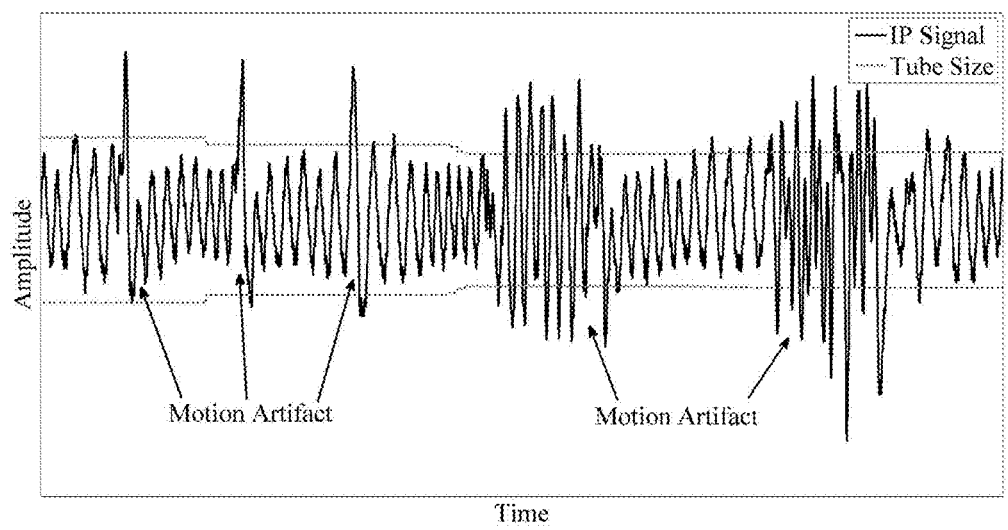
FIG. 6 illustrates an example of a sample portion of an IP signal and a corresponding computed tube size in accordance with an exemplary aspect of the present disclosure.
Figure 7:
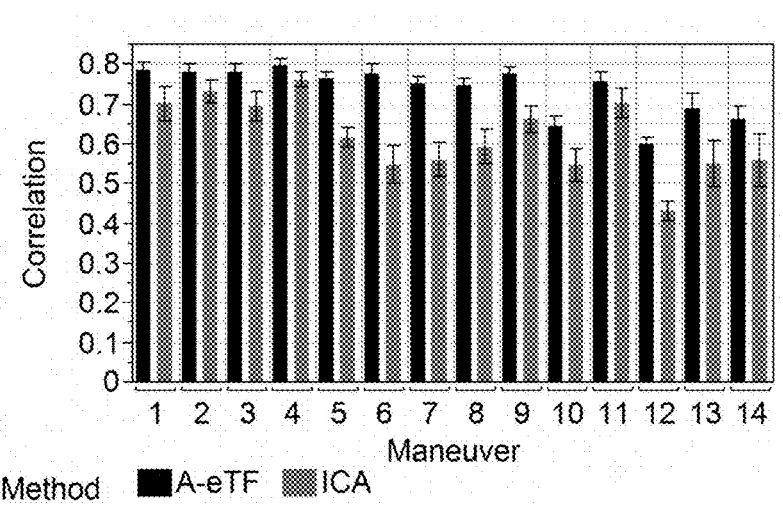
FIG. 7 shows an exemplary comparison between the adaptive ε-tube filter (A-eTF or A-εTF) method and independent component analysis (ICA) method with respect to the correlation measures for individual maneuvers in accordance with an exemplary aspect of the present disclosure.
Figure 8:
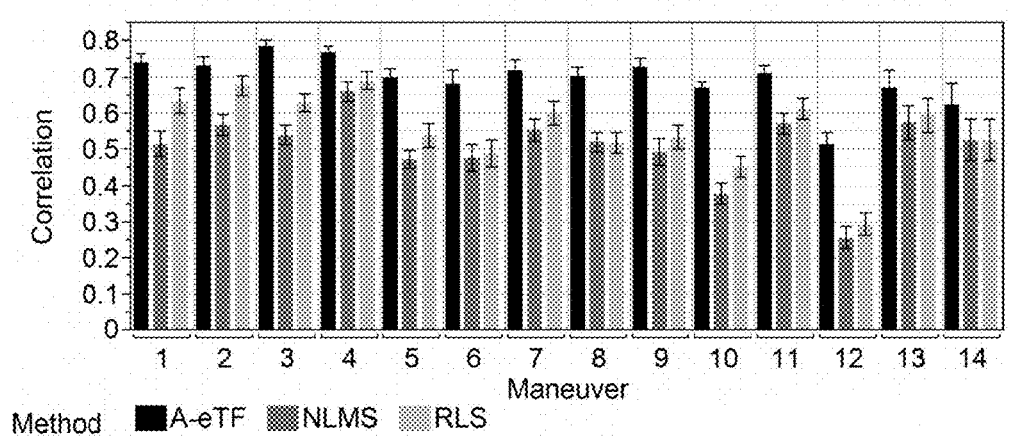
FIG. 8 shows an exemplary comparison between the adaptive ε-tube filter (A-eTF or A-εTF) method, the normalized least mean squares (NLMS) method, and the recursive least squares (RLS) method with respect to the correlation measures for individual maneuvers in accordance with an exemplary aspect of the present disclosure.
Figure 9:
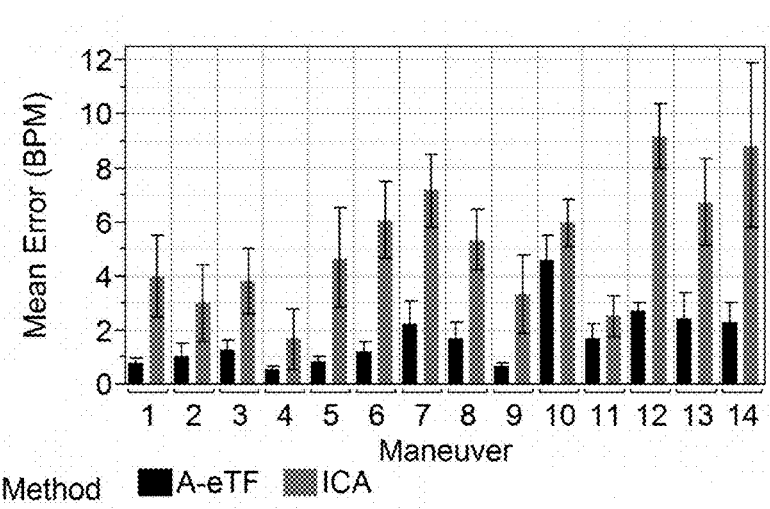
FIG. 9 shows an exemplary comparison between the adaptive ε-tube filter (A-eTF or A-εTF) method and independent component analysis (ICA) method with respect to the mean error performance measures for individual maneuvers in accordance with an exemplary aspect of the present disclosure.
Figure 10:
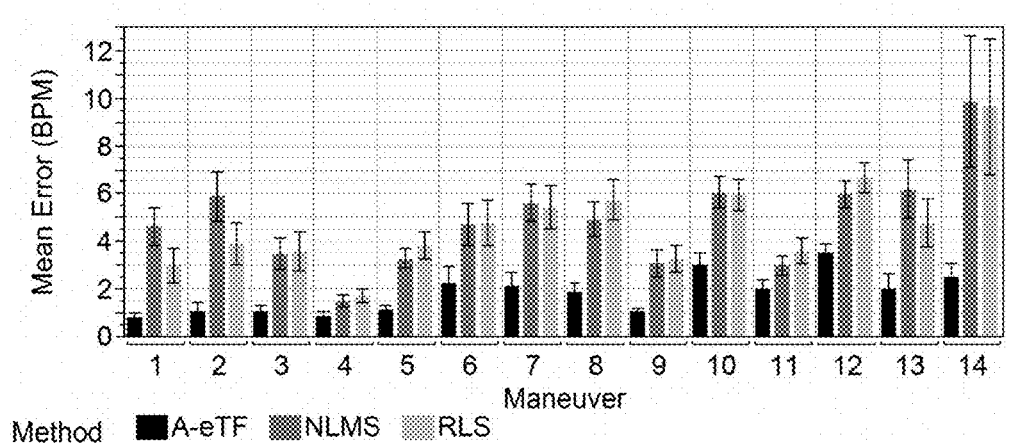
FIG. 10 shows an exemplary comparison between the adaptive ε-tube filter (A-eTF or A-εTF) method, the normalized least mean squares (NLMS) method, and the recursive least squares (RLS) method with respect to the mean error performance measures for individual maneuvers in accordance with an exemplary aspect of the present disclosure.

In an embodiment, the adaptive ε-tube filter may attempt to maintain a margin between the signal and the tube to avoid the tube from becoming too tight. Therefore, continuing the previous example, if the margin between the amplitude of the filtered signal and the tube in a window from t−4T to T is larger than 0.1ε(t), the tube size is adjusted to create a margin between the filtered signal and the tube with a size equal to 0.1ε(t). Otherwise, the size of the tube does not change. An example of a sample portion of the IP signal and the corresponding tube size that is computed using the process that is explained above are shown in FIG. 6.

In an embodiment, the adaptive ε-tube filter may compute $S_{h_1(t)}^{0,\cdot\cdot}$ for each signal sample. Computing ST may be a time consuming process that slows down the adaptive ε-tube filter. However, $S_{h_1(t)}^{0,\cdot\cdot}$ can be computed from $S_{h_1(t-1)}^{0,\cdot\cdot}$ by taking a few steps to eliminate the need for the ST to be explicitly computed.

The vector $h_1(t)$ is obtained by shifting vector $h_1(t-1)$ backwards (circular shift), replacing the value in front of the window (the value that is supposed to leave the window) with the new signal sample that is entering the window, and subtracting the most recent computed filter output y(t−1) from the corresponding signal value g(t−1). The circular shift can be performed using:

$$\mathcal{R}_{h_1(t-1)} = I_{-1} S_{h_1(t-1)} E$$

where $$I_{-1} = \begin{pmatrix} 0_{(2T-1)\times 1} & I_{(2T-1)\times(2T-1)} \\ 1 & 0_{1\times(2T-1)} \end{pmatrix}$$

and E is a diagonal matrix whose $n^{th}$ diagonal value is $$e^{\frac{j2\pi n}{N}}.$$

The rest of the steps can be performed as follows:

$$S_{h_1(t)} = \mathcal{R}_{h_1(t-1)} + [g(t+T)-(g(t-T)-y(t-T))]S_{\delta(x-T)} - y(t-1) S_{\delta(x+1)}.$$

Likewise, the ST that is used to build the prototype (from t−2T−1 to t−1) can be obtained without explicit computation of the ST as follows:

$$S_{h(t-T-1)} = \mathcal{R}_{h_1(t-T-2)} + [(g(t-1)-y(t-1))-g(t-2T-2)-y(t-2T-2))]S_{\delta(x-T)},$$

where $$\mathcal{R}_{h_1(t-T-2)} = I_{-1} S_{h(t-T-2)} E.$$

The adaptive ε-tube filter advantageously outperforms conventional methods to remove blunt noise from periodic signals. Two conventional approaches to remove motion artifacts from periodic physiological signals, such as electrocardiogram and photoplethysmography signals, for example, include independent component analysis (ICA) and adaptive filters such as least mean squares (LMS), recursive least squares (RLS), normalized least mean squares (NLMS), etc., which are considered the most effective methods to remove motion artifacts.

These methods were compared to the adaptive ε-tube filter by applying each one of them to the IP signals that were corrupted by MA. The adaptive ε-tube filter was compared to RLS and NLMS filters using the data that was collected from 13 subjects while the comparison with ICA was done using the data from 7 subjects. Each subject was asked to perform 14 different maneuvers several times, as described in Table 1 below.

TABLE 1

| Maneuver | Description |
|---|---|
| 1 | Raising the arm and holding it up. |
| 2 | Dropping the arm after it was held up for 10 seconds. |
| 3 | Raising the arm and dropping it immediately. |
| 4 | Imitating the act of drinking a cup of water. |
| 5 | Twisting the upper body towards right and back. |
| 6 | Twisting the upper body towards left and back. |
| 7 | Standing up. |
| 8 | Sitting down after 10 seconds. |
| 9 | Imitating the act of opening a window. |
| 10 | Raising the arm and dropping it continuously. |
| 11 | Imitating the act of taking food from a plate and putting it in the mouth continuously. |
| 12 | Twisting the upper body towards right and left continuously. |
| 13 | While standing, imitating the act of walking (in place). |
| 14 | While standing, imitating the act of running (in place). |

The subjects' respiration was monitored using an EtCO2 signal that was measured through a nasal cannula and used as the reference signal. Several different performance measures were computed to compare the adaptive ε-tube filter to ICA, RLS, and NLMS. One of these performance measures is the average correlation between the filtered signal and the reference signal (Corr). Moreover, several measures were based on the error of the respiratory rate that was extracted from the filtered signal compared to the one extracted from the reference signal, including the proportion of instances where the error is smaller than 1 breaths per minute (Dev1), proportion of instances where the error is smaller than 3 breaths per minute (Dev3), the mean error (Mean Err), standard deviation of the error (St.D. Err), and maximum error (Max Err).

The results of the comparisons are shown in Table 2 below, indicating that the adaptive ε-tube filter outperforms the popular existing methods with regards to all the performance measures. Moreover, FIGS. 7-10 show the comparison between the methods with respect to the correlation and mean error performance measures for individual maneuvers. The results indicate that adaptive ε-tube filter has a better performance according to both measures and for all the maneuvers that have been performed. Moreover, statistical tests indicate that out of 42 comparisons against the adaptive ε-tube filter involving the correlation measure, 41 were statistically significant ($\alpha=0.05$). Also, out of 42 comparisons against adaptive ε-tube filter involving the mean error measure, 36 were statistically significant ($\alpha=0.05$). These results suggest that the improvements in the performance that are observed when adaptive ε-tube filter is used are statistically significant.

TABLE 2

| Method | Corr | Dev1 | Dev3 | Mean Err | St. D. Err | Max Err |
|---|---|---|---|---|---|---|
| A ε-TF | 0.702 | 0.706 | 0.864 | 1.750 | 2.644 | 10.315 |
| NLMS | 0.507 | 0.534 | 0.686 | 4.556 | 4.940 | 19.432 |
| RLS | 0.559 | 0.591 | 0.732 | 4.463 | 5.969 | 28.012 |
| A ε-TF | 0.743 | 0.747 | 0.887 | 1.669 | 2.653 | 10.621 |
| ICS | 0.624 | 0.634 | 0.741 | 4.943 | 5.344 | 21.066 |

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A computer-implemented method of adaptively filtering a signal, comprising:
    sampling, by one or more processors, a signal over a plurality of successive sliding time windows, the signal including a primary signal component having an amplitude that varies over time but is substantially constant within each of the plurality of successive sliding time windows;
    receiving, by one or more processors, a plurality of movement signals over a first sliding time window from among the plurality of successive sliding time windows, the plurality of movement signals being indicative of a blunt noise component that is introduced into the signal within the first sliding time window as a motion artifact due to a user's movement, the blunt noise component having a frequency spectrum that overlaps with the received signal;
    calculating, by one or more processors, a prototype signal that models dominant frequency components of the signal from a second sliding time window that chronologically precedes the first sliding time window;
    calculating, by one or more processors, a set of filter coefficients utilizing the plurality of movement signals within the first sliding time window to (i) minimize an objective function associated with frequency error, and (ii) satisfy a constraint associated with the filtered signal amplitude; and
    filtering, by one or more processors, the signal within the first sliding time window in accordance with the set of filter coefficients to retain the primary signal component while removing the blunt noise,
    wherein the constraint is satisfied when the filtered signal amplitude within the first sliding time window is limited between a threshold value based upon the primary signal component amplitude within the second sliding time window, and
    wherein the objective function is minimized when the error between frequency components of the filtered signal within the first sliding time window and the frequency components of the prototype signal are minimized.

2. The computer-implemented method of claim 1, wherein the objective function includes a term such that the amplitude of the filter coefficients are driven towards zero when no blunt noise is detected.

3. The computer-implemented method of claim 1, further comprising:
    repeating the acts of receiving the plurality of movement signals, calculating the set of filter coefficients, and filtering the signal for the plurality of successive sliding time windows to perform real-time signal filtering as the signal is sampled.

4. The computer-implemented method of claim 3, wherein for each of the plurality of successive sliding time windows that are filtered, the constraint is satisfied upon the filtered signal amplitude within each of the plurality of successive sliding time windows being limited between the threshold value for each of the plurality of successive sliding time windows such that the threshold value adapts to changes in signal amplitude over time.

5. The computer-implemented method of claim 4, further comprising:
adjusting, by one or more processors, the threshold value used to determine satisfaction of the constraint for the first sliding time window when the threshold value was exceeded by the amplitude of the filtered signal within the sliding time window.

6. The computer-implemented method of claim 5, wherein the act of adjusting comprises:
adjusting the threshold value only when the blunt noise is determined to not be present in the signal.

7. The computer-implemented method of claim 5, wherein the act of calculating the prototype signal comprises:
calculating the prototype signal only when the blunt noise is determined to not be present in the signal.

8. The computer-implemented method of claim 5, wherein the act of adjusting comprises:
adjusting the threshold value to a new threshold value that is proportional to an amount in which the threshold value was exceeded by the amplitude of the primary component of the signal within the second sliding time window.

9. The computer-implemented method of claim 1, further comprising:
determining, by one or more processors, whether the blunt noise component is present within the first sliding time window based upon a power level of one or more of the plurality of movement signals exceeding a respective threshold power level.

10. The computer-implemented method of claim 9, further comprising:
calculating the set of filter coefficients and filtering the signal only when the blunt noise component is determined to be present.

11. The computer-implemented method of claim 1, wherein:
the signal corresponds to an impedance plethysmography (IP) signal,
the primary signal component corresponds to a respiratory component of the IP signal,
and
the respiratory component of the signal having an amplitude and a frequency that are substantially constant within each of the plurality of successive sliding time windows.

12. The computer-implemented method of claim 1, further comprising:
calculating, by one or more processors, a Stockwell transform of (i) the filtered signal within the first sliding time window and (ii) the prototype signal, to generate the frequency components of the filtered signal within the first sliding time window and the frequency components of the prototype signal.

13. The computer-implemented method of claim 1, wherein the act of calculating the prototype signal comprises;
calculating a piecewise linear approximation of the square of the magnitude of the frequency components of the signal within the second sliding time window.

14. The computer-implemented method of claim 1, wherein the signal includes one or more of the following:
an electrocardiogram;
an impedance cardiograph;
an impedance-based blood volume waveform;
an arterial blood pressure waveform;
a venous blood pressure waveform;
an intracranial pressure waveform;
a photoplethysmography waveform;
an end-tidal carbon dioxide waveform;
a light absorption spectral signal;
a Doppler signal; and
a piezoelectric signal.

15. The computer-implemented method of claim 1, wherein the signal is indicative of a medical diagnostic measurement, and
wherein the plurality of movement signals are indicative of a patient's movement during the medical diagnostic measurement.

16. A data acquisition system configured to adaptively filter a medical diagnostic signal representative of a patient's biological process, comprising:
a data acquisition module configured to (i) sample the signal over a plurality of successive sliding time windows, the signal including a respiratory signal component having an amplitude that varies within a tube that imposes a limit on the amplitude of the signal, and (ii) receive a plurality of movement signals over a first sliding time window from among the plurality of successive sliding time windows, the plurality of movement signals being indicative of a blunt noise component that is introduced into the signal within the first sliding time window as a motion artifact due to the patient's movement, the blunt noise component having a frequency spectrum that overlaps with the received signal;
a filter coefficient calculation module configured to (i) calculate a prototype signal based upon dominant frequency components of the signal from a second sliding time window that chronologically precedes the first sliding time window, and (ii) calculate a set of filter coefficients utilizing the plurality of movement signals within the first sliding time window to minimize an objective function associated with frequency error and satisfy a constraint associated with the filtered signal amplitude; and
a filtering module configured to filter the signal within the first sliding time window in accordance with the set of filter coefficients to retain the respiratory signal component while removing the blunt noise,
wherein the constraint is satisfied when the filtered signal amplitude within the first sliding time window is limited between a threshold value based upon the primary signal component amplitude within the first sliding time window, and
wherein the objective is optimized when the error between frequency components of the filtered signal within the first sliding time window and the frequency components of the prototype signal are minimized.

17. The data acquisition system of claim 16, wherein the objective function includes a term such that the amplitude of the filter coefficients are driven towards zero when no blunt noise is detected.

18. The data acquisition system claim 16, wherein the data acquisition module, the filter coefficient calculation module, and the filtering module are further configured to receive the plurality of movement signals, to calculate the set of filter coefficients, and to filter the signal over the plurality of successive sliding time windows to perform real-time signal filtering as the signal is sampled.

19. The data acquisition system claim 18, wherein for each of the plurality of successive sliding time windows that are filtered, the constraint is satisfied upon the filtered signal amplitude within each of the plurality of successive sliding time windows being limited between the threshold value for each of the plurality of successive sliding time windows such that the threshold value adapts to changes in signal amplitude over time.

20. The data acquisition system of claim 19, wherein the filter coefficient calculation module is further configured to adjust the threshold value used to determine satisfaction of the constraint for the first sliding time window when the threshold value was exceeded by the amplitude of the primary component of the signal within the second sliding time window.

21. The data acquisition system of claim 20, wherein the filter coefficient calculation module is further configured to adjust the threshold value only when the blunt noise is determined to not be present in the signal.

22. The data acquisition system of claim 20, wherein the filter coefficient calculation module is further configured to calculate the prototype signal only when the blunt noise is determined to not be present in the signal.

23. The data acquisition system of claim 20, wherein the filter coefficient calculation module is further configured to adjust the threshold value to a new threshold value that is proportional to an amount in which the threshold value was exceeded by the amplitude of the primary component of the signal within the second sliding time window.

24. The data acquisition system claim 16, wherein the filter coefficient calculation module is further configured to determine whether the blunt noise component is present within the first sliding time window based upon a power level of one or more of the plurality of movement signals exceeding a respective threshold power level.

25. The data acquisition system of claim 24, wherein the filter coefficient calculation module is further configured to calculate the set of filter coefficients and filtering the signal only when the blunt noise component is determined to be present.

26. The data acquisition system of claim 16, wherein the signal corresponds to an impedance plethysmography (IP) signal, and wherein the respiratory component of the IP signal has a frequency and amplitude that are substantially constant within each of the plurality of successive sliding time windows.

27. The data acquisition system of claim 16, further comprising:
a regularization module configured to calculate (i) a Stockwell transform of the filtered signal within the first sliding time window, (ii) a Stockwell transform of the prototype signal, and (iii) the frequency components of the filtered signal within the first sliding time window and the frequency components of the prototype signal based upon (i) and (ii), respectively.

28. The data acquisition system of claim 16, wherein the regularization module is further configured to calculate the prototype signal based upon a piecewise linear approximation of the square of the magnitude of the frequency components of the signal within the second sliding time window.

29. The data acquisition system of claim 16, wherein the signal includes one or more of the following:
an electrocardiogram;
an impedance cardiograph;
an impedance-based blood volume waveform;
an arterial blood pressure waveform;
a venous blood pressure waveform;
an intracranial pressure waveform;
a photoplethysmography waveform;
an end-tidal carbon dioxide waveform;
a light absorption spectral signal;
a Doppler signal; and
a piezoelectric signal.

30. The data acquisition system of claim 16, wherein the signal is indicative of a medical diagnostic measurement, and
wherein the plurality of movement signals are indicative of a patient's movement during the medical diagnostic measurement.

* * * * *